(12) United States Patent
Dacosta et al.

(10) Patent No.: US 11,076,864 B2
(45) Date of Patent: Aug. 3, 2021

(54) TISSUE REMOVAL INSTRUMENT

(71) Applicant: Paragon 28, Inc., Englewood, CO (US)

(72) Inventors: Albert Dacosta, Lone Tree, CO (US); Frank S. Bono, Castle Rock, CO (US); Benjamin Majors, Englewood, CO (US); Laura Zagrocki Brinker, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 173 days.

(21) Appl. No.: 16/185,765

(22) Filed: Nov. 9, 2018

(65) Prior Publication Data
US 2019/0083108 A1 Mar. 21, 2019

Related U.S. Application Data

(63) Continuation of application No. PCT/US2017/032654, filed on May 15, 2017.
(Continued)

(51) Int. Cl.
*A61B 17/16* (2006.01)
*A61B 17/285* (2006.01)
(Continued)

(52) U.S. Cl.
CPC ...... *A61B 17/1606* (2013.01); *A61B 17/1682* (2013.01); *A61B 17/282* (2013.01);
(Continued)

(58) Field of Classification Search
CPC ............ A61B 17/1606; A61B 17/1682; A61B 17/8866; A61B 17/2804; A61B 17/282;
(Continued)

(56) References Cited

U.S. PATENT DOCUMENTS 1,363,164 A * 12/1920 Oesterwitz ............. A45D 29/02
30/28
2,476,895 A * 7/1949 Muter ....................... B25B 7/12
606/136
(Continued)

FOREIGN PATENT DOCUMENTS

DE         20207785         9/2003

OTHER PUBLICATIONS

International Search Report and Written Opinion of the International Searching Authority for PCT/US2017/032654, dated Aug. 3, 2017, 10 pages.
(Continued)

*Primary Examiner* — Kevin T Truong
*Assistant Examiner* — Tracy L Kamikawa
(74) *Attorney, Agent, or Firm* — Heslin Rothenberg Farley & Mesiti P.C.; Kristian E. Ziegler, Esq.

(57) ABSTRACT

Resected bone and/or tissue removal instruments and related methods are disclosed. The instruments include a first elongate member including a first head portion with a front edge and a first handle portion. The instrument further includes second elongate member rotatably coupled to the first elongate member at a first rotation point, the second member including a second handle portion and an end portion. The instrument also includes a third elongate member rotatably coupled to the first elongate member at a second rotation point, the third member including a second head portion and an end portion. The end portions of the second and third members are rotatably coupled at a third movable rotation point positioned between the first and second rotation points. The second head portion includes an interior surface with a front cutting tooth defining a free end of the second head portion.

26 Claims, 12 Drawing Sheets

Related U.S. Application Data

(60) Provisional application No. 62/335,741, filed on May 13, 2016.

(51) Int. Cl.
*A61B 17/28* (2006.01)
*A61B 17/88* (2006.01)

(52) U.S. Cl.
CPC ........ *A61B 17/2804* (2013.01); *A61B 17/285* (2013.01); *A61B 17/8866* (2013.01)

(58) Field of Classification Search
CPC .............. A61B 17/285; A61B 17/1608; A61B 17/1611
See application file for complete search history.

(56) References Cited

U.S. PATENT DOCUMENTS

| | | | | |
|---|---|---|---|---|
| 2,994,321 | A * | 8/1961 | Tischler | A61B 17/32 600/564 |
| 3,391,690 | A * | 7/1968 | Armao | A61B 18/02 600/564 |
| 4,462,403 | A * | 7/1984 | Martin | A61B 17/1606 30/190 |
| 4,597,385 | A * | 7/1986 | Watson | A61B 10/0291 600/564 |
| 6,702,820 | B2 | 3/2004 | Mazur | |
| 6,706,048 | B2 * | 3/2004 | Hermann | A61B 17/0643 606/139 |
| 7,625,391 | B2 * | 12/2009 | Kebel | A61B 17/28 606/203 |
| 8,308,738 | B2 | 11/2012 | Nobis et al. | |
| 8,768,435 | B2 * | 7/2014 | Andrus | A61M 3/02 600/424 |
| 9,066,744 | B2 | 6/2015 | Kalmann et al. | |
| 2004/0024319 | A1 * | 2/2004 | Flipo | A61B 17/2804 600/459 |
| 2006/0135959 | A1 * | 6/2006 | Yuan | A61B 17/1606 606/83 |
| 2006/0173452 | A1 | 8/2006 | Buysse et al. | |
| 2010/0274358 | A1 * | 10/2010 | Mueller | A61B 17/7059 623/17.16 |
| 2012/0016401 | A1 | 1/2012 | Faulhaber et al. | |
| 2012/0197248 | A1 | 8/2012 | Truckai et al. | |
| 2013/0245421 | A1 | 9/2013 | Andrus et al. | |

OTHER PUBLICATIONS

Extended European Search Report issued in corresponding European Patent Application No. EP 17797021.7 dated Dec. 12, 2019.

* cited by examiner

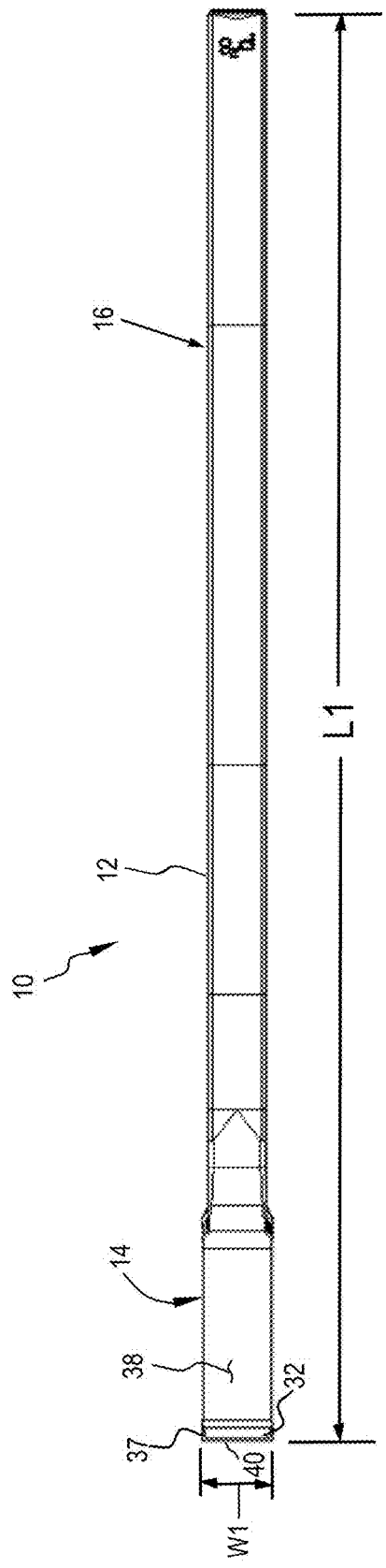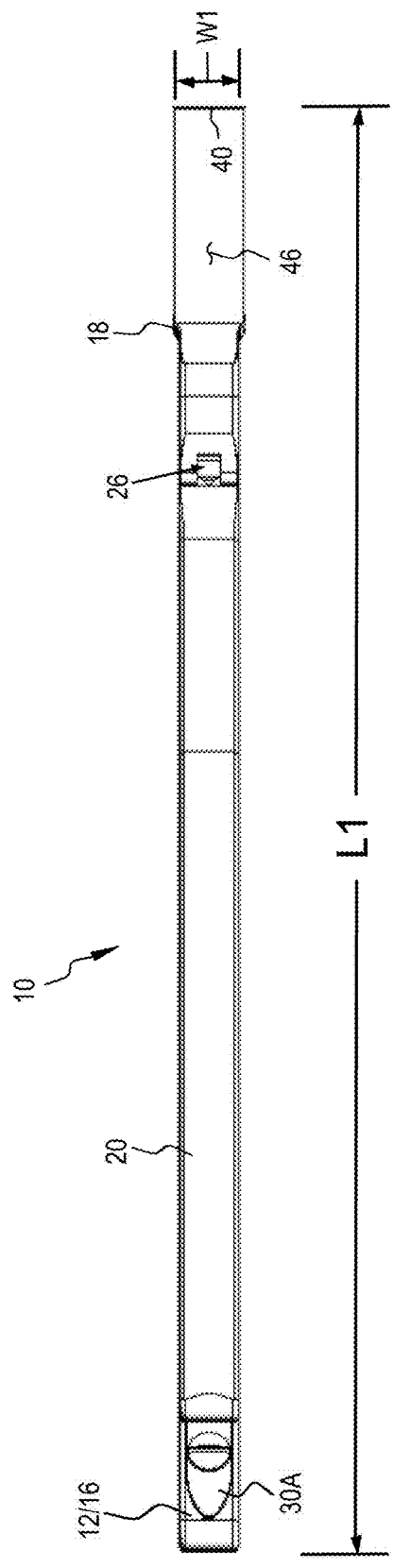

TISSUE REMOVAL INSTRUMENT

CROSS-REFERENCE TO RELATED APPLICATION

This application is a continuation of PCT Application No. PCT/US2017/032654 filed on May 15, 2017, which claims priority benefit under 35 U.S.C. § 119(e) of U.S. Provisional Application No. 62/335,741 filed on May 13, 2016, which is entitled Bone Removal Instrument, and which is incorporated herein by reference in its entirety.

FIELD OF THE INVENTION

The present disclosure is generally directed to instruments and related methods for bone and/or tissue removal. More particularly, the present disclosure is directed to handheld resected bone and/or tissue removal instruments and related methods for removing a resected bone portion from a patient.

BACKGROUND OF THE INVENTION

A bone or tissue may be resected (i.e., the excision of a portion of the bone) in any number of ways for any number of reasons. For example, adjacent portions of two or more bones or tissue forming a joint therebetween may be resected, and the bones may be reduced to promote fusion of the bones. As another example, during an arthrodesis procedure an artificial induction of joint ossification between two bones may be achieved, in part, by resecting adjacent portions of the two bones. In a Lapidus Arthrodesis procedure, for example, the base portion of the first metatarsal and a portion of the medial cuneiform are resected to promote fusion of the first metatarsal and the medial cuneiform.

A bone may be resected using a device that cuts through the bone to separate a portion therefrom, and subsequent removal of the portion from the patient. For example, a sagittal or reciprocating saw may be used to cut through a bone to segment the bone. A resected portion of a bone (i.e., a separated portion of the bone that will be removed from the patient) may include cartilage, ligaments, tendons or other tissue connected to the resected portion. Such tissue, if present, may be resected or disconnected either before or after the resected bone portion is separated from the remaining portion of the bone. This tissue is relatively difficult to remove from the resected bone portion, and thus makes removal of the resected bone portion difficult. A sagittal saw, curette, burr, scalpel blade, osteotome, scissors or other device is typically used to resect such tissue. The resected bone portion may thereby include some of such tissue connected thereto after resection.

Typical methods of removing a resected bone portion include the manual use of a tool, such as a rongeur, curette, osteotome and/or hemostat, to physically engage the portion and extract the portion from the patient. However, removal of a resected bone portion may be relatively difficult. For example, the resected bone portion may be positioned in a relatively tight, flat joint space which restricts access to the resected bone portion. As another example, the resected bone portion may be attached to at least one tendon, ligament or other soft tissue that is relatively difficult to resect or otherwise makes removal of the resected bone portion challenging. As yet another example, the resected bone portion may be in a form of a relatively thin wafer that is prone to breakage by the removal tool, thereby requiring many attempts to remove broken pieces of the resected portion.

Therefore, bone and/or tissue removal instruments and related methods that fit into tight spaces or joints, adequately remove soft tissue from resected bone or tissue portions, and securely engage resected bone or tissue wafers to prevent breakage thereof are desirable.

SUMMARY OF THE INVENTION

In one aspect, the present disclosure provides for a resected bone portion removal instrument. The instrument includes a first elongate member, a second elongate member and a third elongate member. The first elongate member includes a first head portion and a first handle portion defining a free end, the first head portion including a substantially flat interior bone engagement surface and a chisel edge defining a free end of the first head portion. The second elongate member is rotatably coupled to the first elongate member at a first rotation point, the second member including a second handle portion defining a free end and an end portion on opposing sides of the first rotation point. The third elongate member is rotatably coupled to the first elongate member at a second rotation point, the third member including a second head portion and an end portion on opposing sides of the second rotation point. The end portions of the second and third members are rotatably coupled at third rotation point positioned between the first and second rotation points. The second head portion includes an interior surface with a front cutting tooth defining a free end of the second head portion, a substantially flat bone engagement surface, and gripping teeth extending between the front cutting tooth and the bone engagement surface.

In another aspect, the present disclosure provides for a method of removing a resected bone portion. The method includes obtaining a bone removal instrument that includes first and second handle portion and first and second head portions, the first and second handle portions configured to effectuate relative movement of the first and second head portions between an open orientation and a closed orientation. The method further includes orienting the first and second head portions of the instrument into the open configuration via the first and second handle portions. The method also includes inserting one of the first head portion or the second head portion between a resected bone portion and a parent bone portion within a patient such that the resected bone portion is positioned between the first and second head portions of the instrument. The method further includes orienting the first and second head portions of the instrument toward the closed orientation via the first and second handle portions to cut tissue extending from the resected bone portion via a cutting tooth of the second head portion and to engage and support the resected bone portion via interior surfaces of the first and second head portions. The method also includes manually removing the instrument and the resected bone portion from the patient.

In another aspect, the present disclosure provides a surgical instrument. The surgical instrument includes a first elongate member including a first head portion and a first handle portion defining a free end, the first head portion includes a front edge defining a free end of the first head portion. The surgical instrument also includes a second elongate member rotatably coupled to the first elongate member at a first rotation point, the second member including a second handle portion defining a free end and an end portion on opposing sides of the first rotation point. The surgical instrument further includes a third elongate member rotatably coupled to the first elongate member at a second rotation point, the third member including a second head portion and an end portion on opposing sides of the second rotation point. The end portions of the second and third members are rotatably coupled at a third movable rotation point positioned between the first and second rotation points. The second head portion includes an interior surface with a front cutting tooth defining a free end of the second head portion.

In some embodiments, the first head portion includes a substantially smooth interior tissue engagement surface extending from the front edge. In some embodiments, the front edge is formed between the interior tissue engagement surface and a chisel portion extending from the interior tissue engagement surface at an acute angle, and the interior tissue engagement surface, the chisel portion and the front edge forming a chisel tooth with the front edge being the tip of the chisel tooth. In some such embodiments, the interior tissue engagement surface is substantially planar. In some other such embodiments, the interior tissue engagement surface is arcuate and curves toward the second head portion as it extends toward the front edge.

In some embodiments, the interior surface of the second head portion includes a substantially smooth tissue engagement surface and a plurality of teeth extending between the front cutting tooth and the tissue engagement surface. In some such embodiments, the front cutting tooth is taller than the plurality of teeth. In some embodiments, the second head portion extends further from the second rotation point than the first head portion. In some such embodiments, the length of the second head portion is within the range of 10 mm and 60 mm. In some embodiments, the first and second head portions define a width within the range of 5 mm and 20 mm. In some embodiments, the first head portion defines a thickness within the range of 0.5 mm and 5 mm, and the front cutting tooth of the second head portion defines a thickness within the range of 2 mm and 6 mm.

In some embodiments, in a fully closed relative position of the first and second handle portions, the front edge abuts the second head portion. In some such embodiments, in the fully closed relative position of the first and second handle portions, the first and second head portions form a gap therebetween that enlarges as it extends from the front edge toward the second rotation point. In some embodiments, the front cutting tooth includes a front face that defines the free end of the second head portion, a cutting edge and a relief surface that extends from the cutting edge an acute angle with respect to the front face. In some such embodiments, in a fully closed relative position of the first and second handle portions, the front edge abuts the relief surface of the front cutting tooth.

In some embodiments, in an open relative position of the first and second handle portions, the front edge is spaced from the front cutting tooth a distance within the range of 3 mm and 20 mm. In some such embodiments, the instrument further includes a biasing mechanism that biases the first and second handle portions into the open position in a neutral state of the instrument. In some embodiments, the movable rotation point is formed via a pin member extending through an aperture of one of the end portions of the second and third members and a slot of the other of the end portions.

In another aspect, the present disclosure provides for a method of removing a resected tissue portion from a body. The method includes obtaining a tissue removal instrument that includes first and second handle portions and first and second head portions, the first and second handle portions configured to effectuate relative movement of the first and second head portions between an open position and a closed position. The method also includes orienting the first and second head portions of the instrument into the open configuration via the first and second handle portions. The method further includes inserting one of the first head portion or the second head portion between a resected tissue portion and a host tissue portion within the body such that the resected tissue portion is positioned between the first and second head portions of the instrument. The method also includes orienting the first and second head portions of the instrument toward the closed orientation via the first and second handle portions to cut tissue extending from the resected tissue portion via a front edge of the first head portion and a cutting tooth of the second head portion and to engage and support the resected tissue portion via interior surfaces of the first and second head portions. The method further includes manually removing the instrument and the resected tissue portion from the body.

In some embodiments, the first head portion includes a substantially smooth interior tissue engagement surface extending from the front edge. In some embodiments, the front edge of the first head portion is formed between the interior surface and a chisel portion extending from the interior surface of the first head portion at an acute angle, and the interior surface, the chisel portion and the front edge of the first head portion form a chisel tooth with the front edge being the tip of the chisel tooth. In some embodiments, the interior surface of the second head portion includes a substantially flat tissue engagement surface and plurality of teeth extending between the front cutting tooth and the tissue engagement surface.

In some embodiments, the resected tissue portion is a bone wafer. In some such embodiments, the host tissue is a $1^{st}$ metatarsal bone. In some such embodiments, the cut tissue includes a tibialis anterior tendon. In some embodiments, the interior surface of the first head portion includes a substantially smooth portion and the interior surface of the second head portion includes plurality of teeth, and the substantially smooth portion of the first head portion and the plurality of teeth of the second head portion engage and support the resected tissue portion.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the bone removal instrument and related methods described herein, there is shown herein illustrative embodiments. These illustrative embodiments are in no way limiting in terms of the precise arrangement and operation of the disclosed bone removal instrument and related methods and other similar embodiments are envisioned within the spirit and scope of the present disclosure.

FIG. 6 is a top view of the bone removal instrument of FIG. 1;

FIG. 7 is a bottom view of the bone removal instrument of FIG. 1;

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 8:
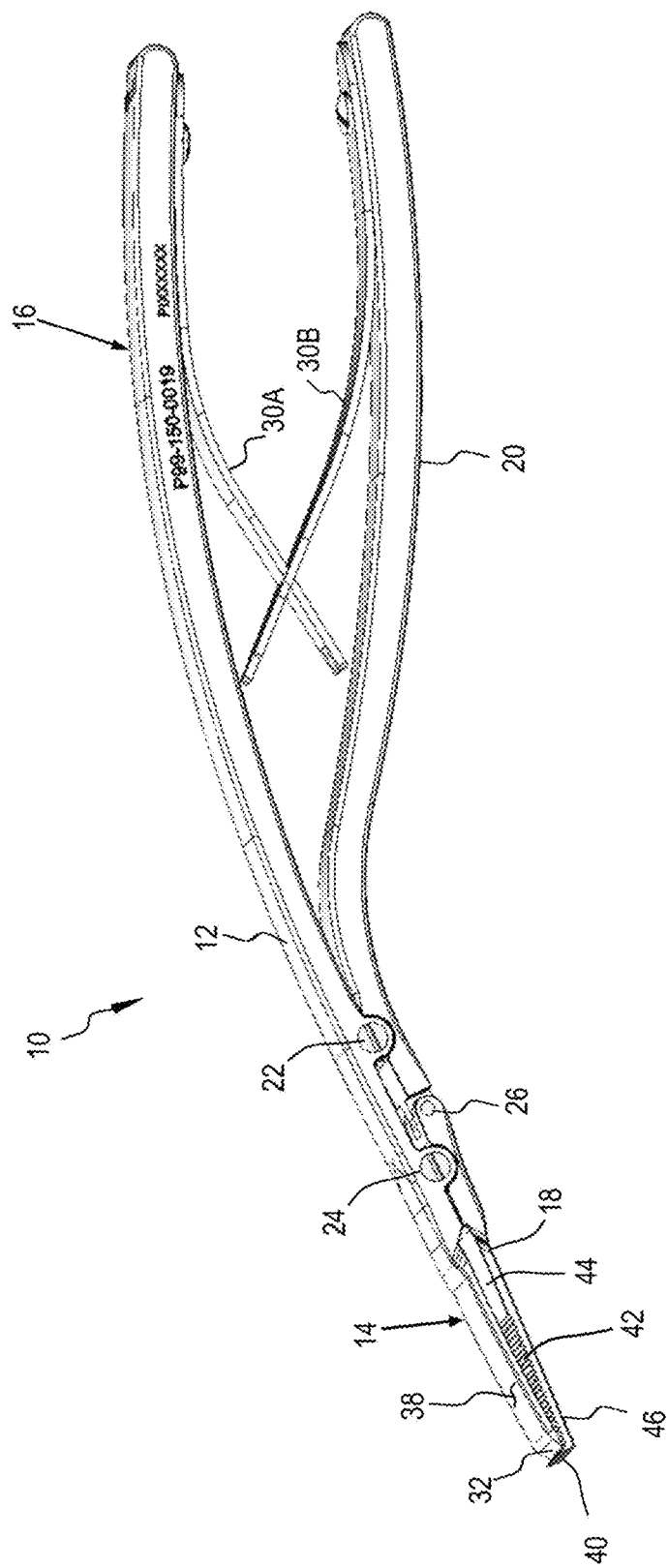
FIG. 8 is an elevational perspective view of the bone removal instrument of FIG. 1 with the head portion thereof in an closed configuration according to the present disclosure.
Figure 9:
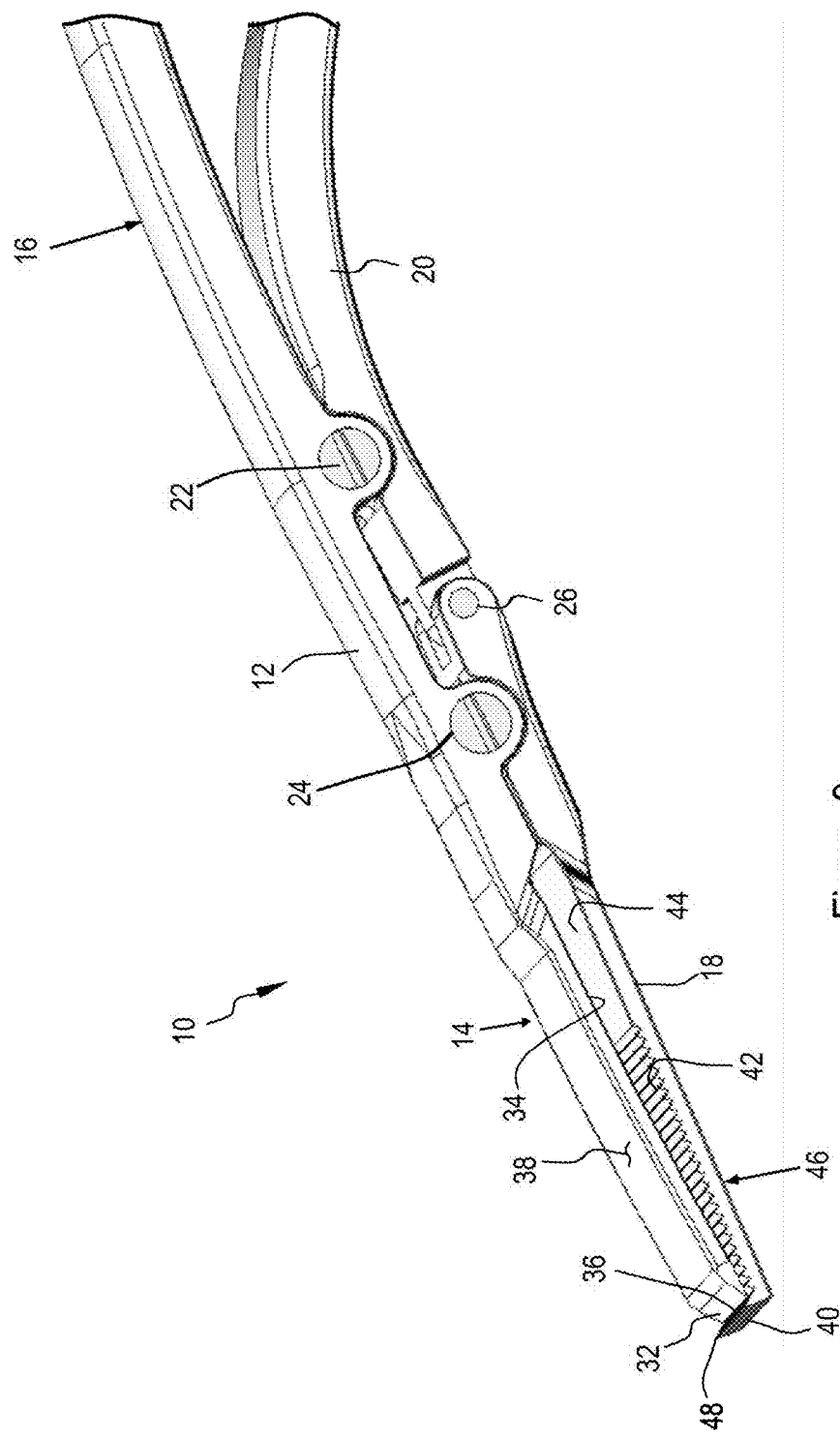
FIG. 9 is an enlarged elevational perspective view of the head portion of the bone removal instrument of FIG. 8.
Figure 10:
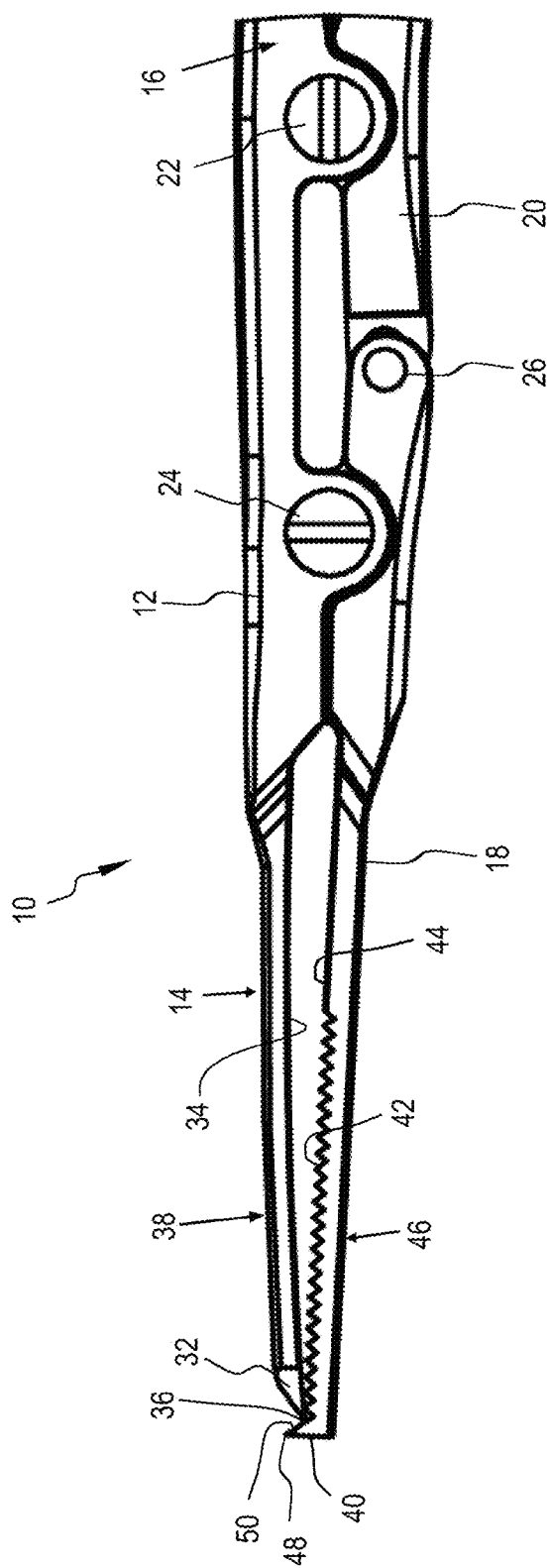
FIG. 10 is an enlarged side view of the head portion of the bone removal instrument of FIG. 9.

As shown in FIGS. 1-10, a bone removal instrument 10 for bone and/or tissue resection according to the present disclosure may be configured as a manual hand-held tool. The instrument 10 may include a first elongate member 12 including a first head portion 14 and a first handle portion 16. The instrument 10 may also include a second elongate member 20 forming a second handle portion, and a third elongate member forming a second head portion 18. As explained further below, relative movement (e.g., rotational movement) of the first handle portion 16 and the second handle member or portion 20 (e.g., via manual manipulation thereof) effectuates relative movement of the first head portion 14 and the second head portion 18 and configuration of the instrument 10 into an open configuration as shown in FIGS. 1-7 or closed configuration as shown in FIGS. 8-10. The second elongate member 20 forming a second handle portion and the third elongate member forming a second head portion 18 may be aligned or arranged end to end along a length direction, and aligned in a thickness and width direction with the first elongate member 12. The instrument 10 itself may thereby be elongate in a length direction and narrow in a width direction. In some embodiments, the instrument 10 may define a length L1 as shown in FIG. 7 within the range of about 5 inches and 12 inches. In an embodiment particularly well suited or advantageous for removing resecting bone and/or tissue during a Lapidus Arthrodesis procedure, for example, the instrument 10 may define a length L1 of about 8 inches.

Figure 1:
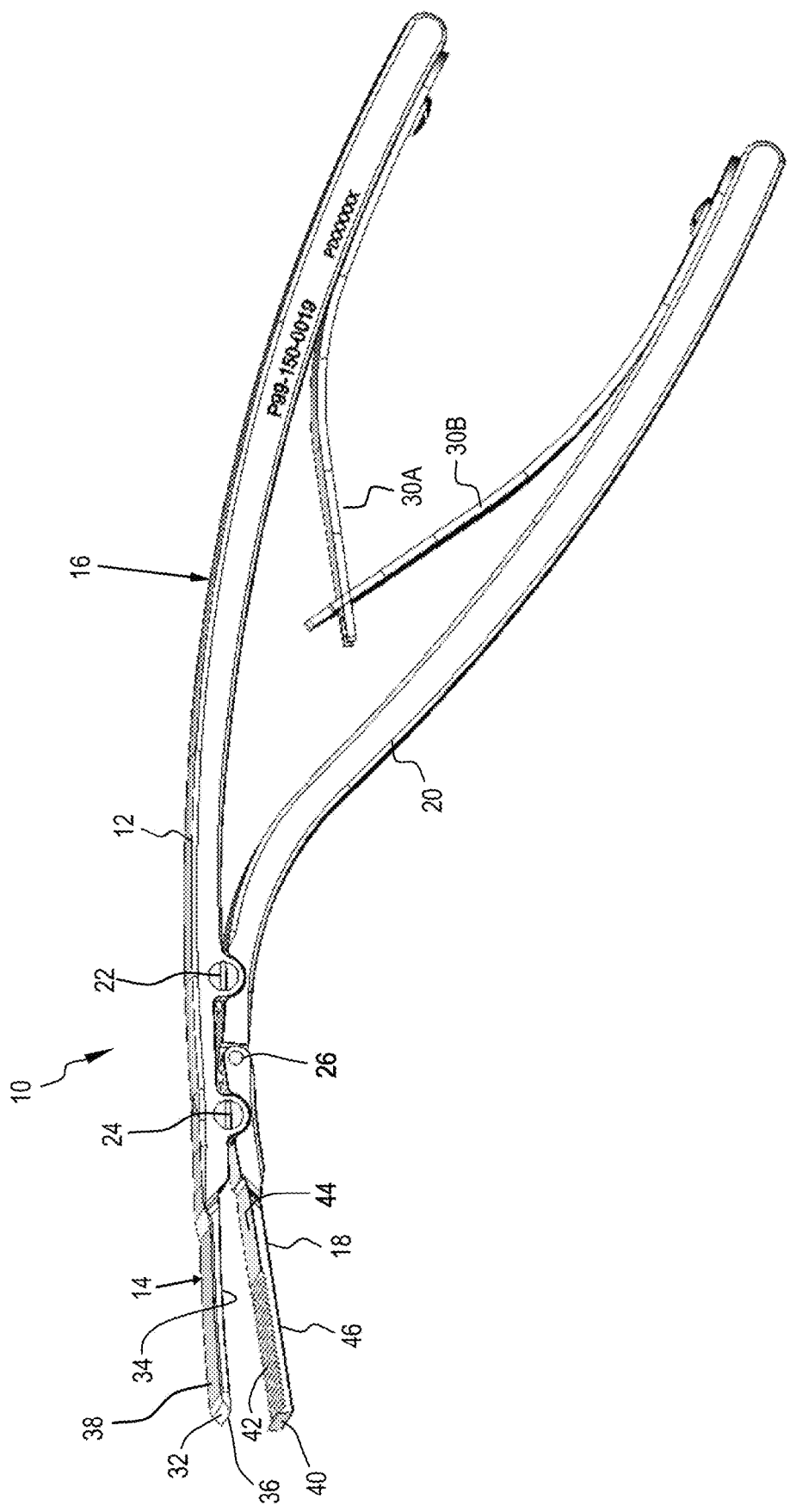
FIG. 1 is an elevational perspective view of a bone removal instrument according to the present disclosure with a head portion thereof in an open configuration.
Figure 2:
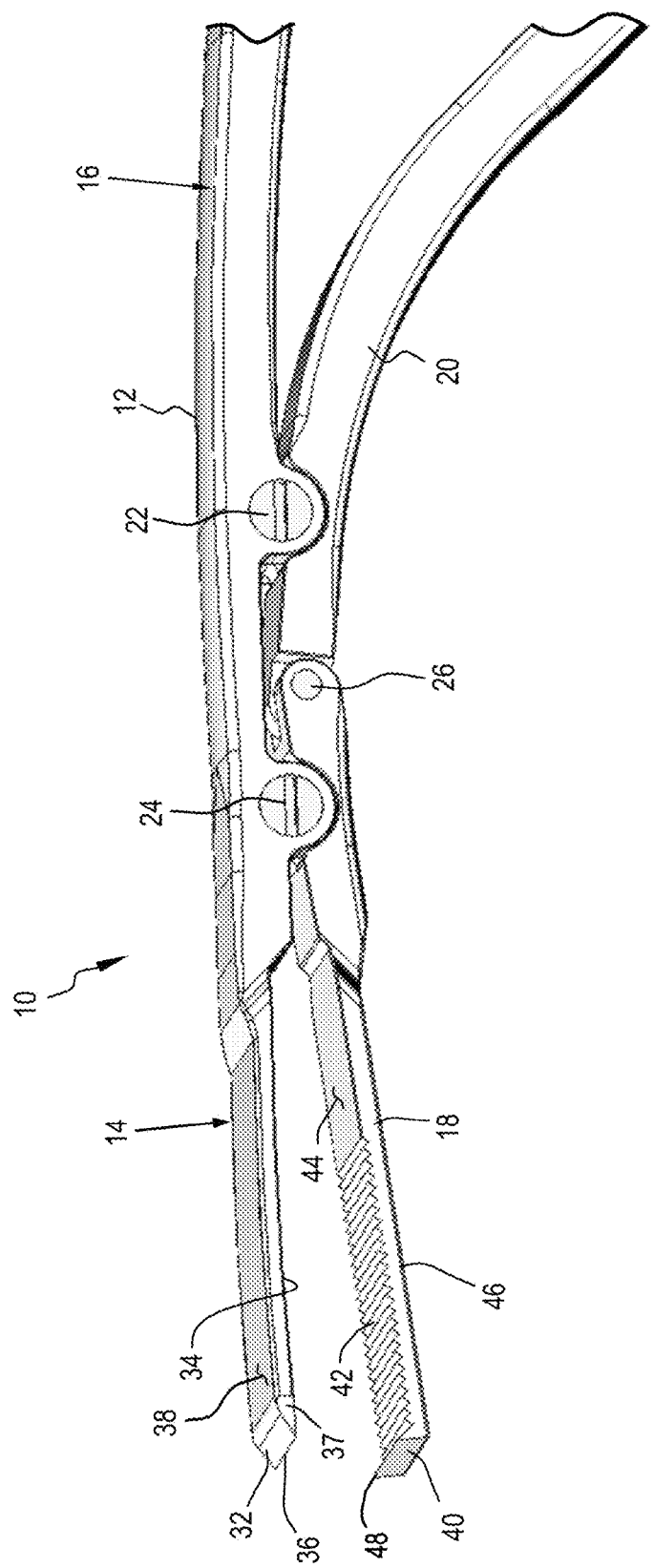
FIG. 2 is an enlarged elevational perspective view of the head portion of the bone removal instrument of FIG. 1.
Figure 3:
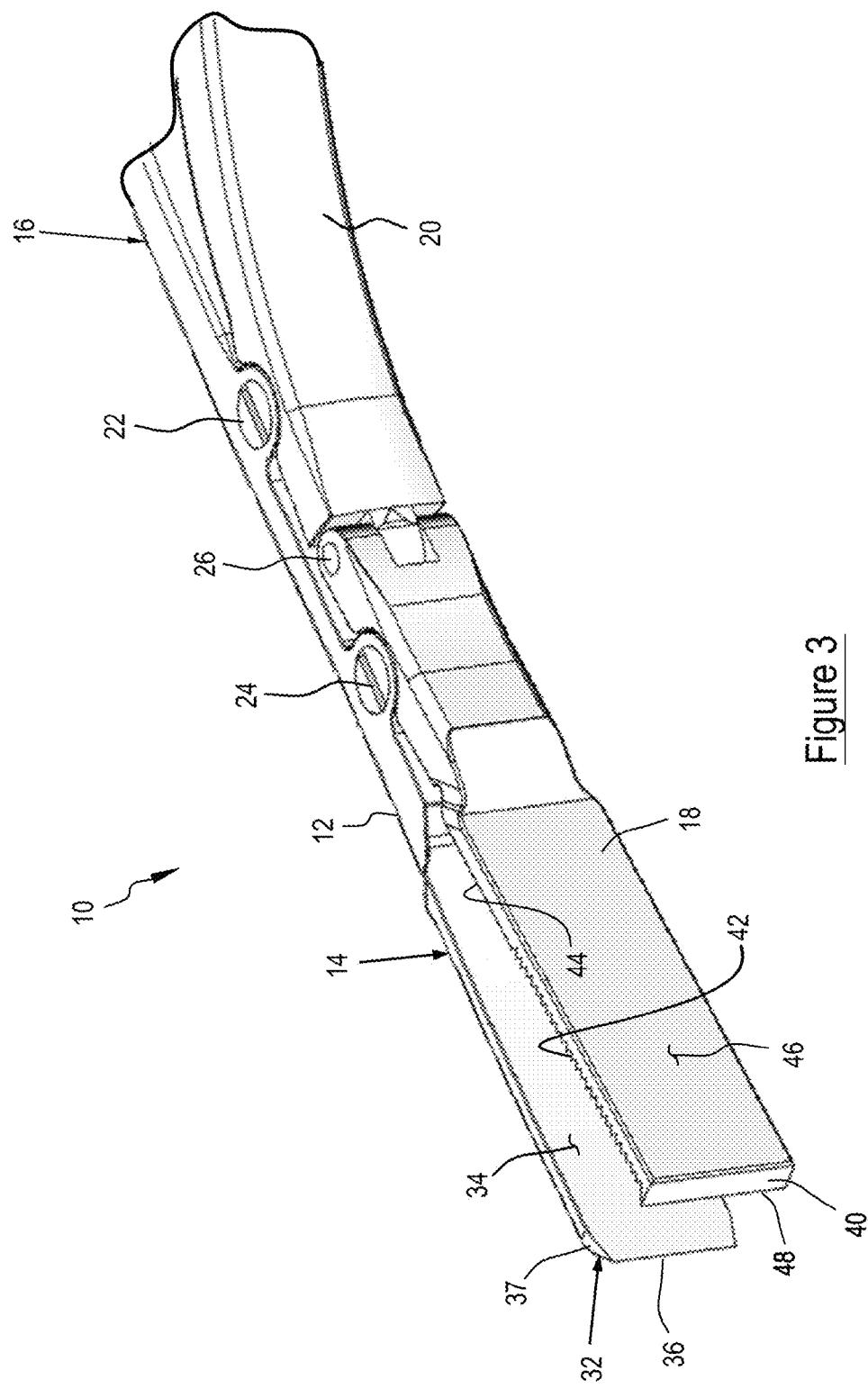
FIG. 3 is an enlarged bottom perspective view of the head portion of the bone removal instrument of FIG. 1.
Figure 4:
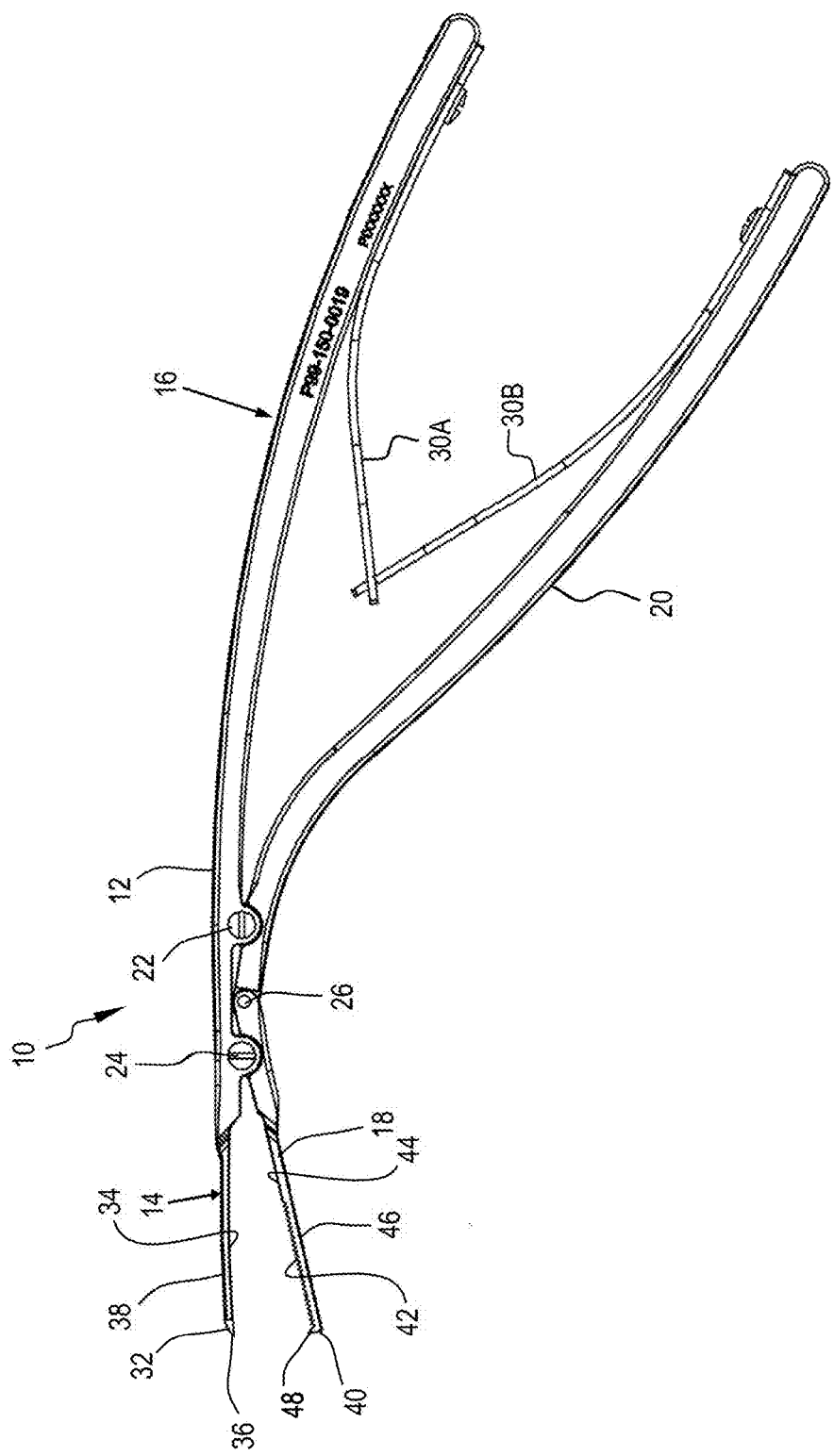
FIG. 4 is a side view of the bone removal instrument of FIG. 1.

The first and second handle portions 16, 20 may define free ends and exterior and interior surfaces. The first and second handle portions 16, 20 may be arcuate and/or concave toward the interior surfaces, as shown in FIGS. 1, 4 and 8. The interior surfaces of the first and second handle portions 16, 20 may face toward each other, and the exterior surfaces of the first and second handle portions 16, 20 may face away from each other. At least proximate to the free ends, the first and second handle portions 16, 20 may be spaced apart along a first direction extending about an axis of rotation or pivot point 22, as explained further below. The portions of the first and second handle portions 16, 20 proximate to the free ends thereof may be spaced about the axis or point of rotation 22 in the open configuration and, potentially, the closed configuration of the instrument 10.

The instrument 10 may include a biasing mechanism that biases the instrument 10 into the open configuration such that the natural or neutral state of the instrument 10 is the open configuration, as shown in FIGS. 1-7. For example, as shown in FIGS. 1 and 4, the interior surfaces of the first and second handle portions 16, 20 may include corresponding flex-spring members 30A, 30B of a cantilever type that mate with each other. The flex-spring members 30A, 30B may be configured to naturally bias or position the first and second handle portions 16, 20 in their open configuration to naturally bias or position the first and second head portions 14, 18 in their open configuration, as shown in FIGS. 1 and 4.

As shown in FIGS. 1, 4 and 8, a portion of the second handle portion 20 that is positioned proximate to an end thereof that opposes the free end may be rotatably or pivotally coupled to an intermediate portion of the first member 12 at the rotation or pivot point 22. The second handle portion 20 may be rotatably or pivotally coupled to the first member 12 between the first head portion 14 and the first handle portion 16. The second handle portion 20 and the first member 12 may be rotatably coupled at the rotation or pivot point 22 via any mechanism. For example, the second handle portion 20 and the first member 12 may be rotatably coupled via a screw, pin or like mechanism that extends through nested or aligned apertures of the second handle portion 20 and the first member 12, as shown in FIGS. 1-4 and 7-10. However, any other mechanism may be employed to rotatably or pivotally couple the second handle portion 20 and the first member 12.

As shown in FIGS. 1-4 and 8-12, an end portion of the second handle portion 20 may extend past the rotation or pivot point 22 in a direction extending away from the free end thereof. As also shown in FIGS. 1-4 and 8-12, the end portion of the second handle portion 20 that is past or spaced from the rotation or pivot point 22 (i.e., on an opposing side of the rotation or pivot point 22) as compared to the free end thereof may be movably (e.g., translatably and/or rotatably or pivotally) coupled to an end portion of the second head portion 18 at a sliding rotation or pivot point 26. The second handle portion 20 and the second head portion 18 may be movably coupled at the sliding rotation or pivot point 26 via any mechanism, including for example a pin member positioned inside an enlarged opening.

Figure 11:
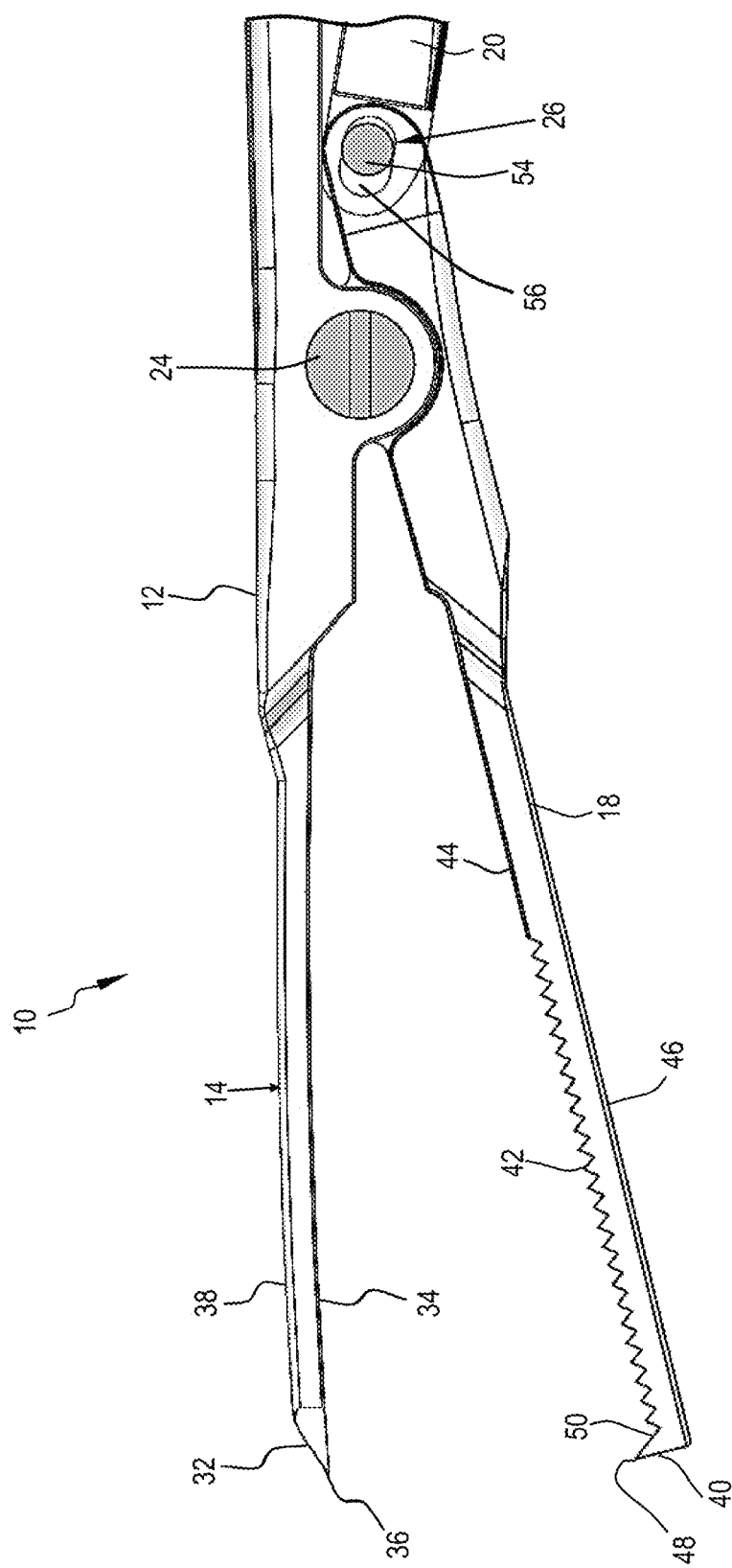
FIG. 11 is an enlarged side view illustrating a sliding pivot point of the bone removal instrument of FIG. 1 with the head portion thereof in an open configuration.
Figure 12:
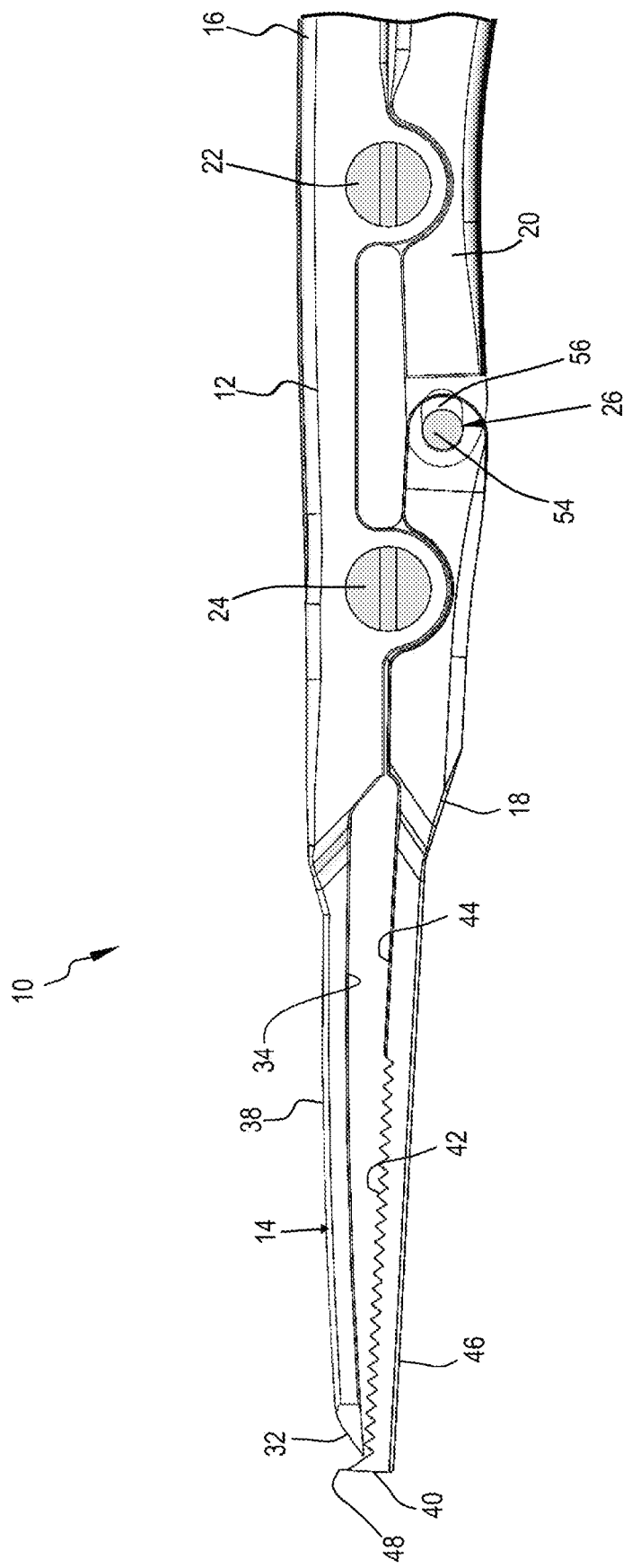
FIG. 12 is an enlarged side view illustrating the sliding pivot point of FIG. 11 with the head portion of the bone removal instrument in a closed configuration.

Any mechanism may be employed to translatably and/or rotatably couple the second handle portion 20 and the second head portion 18 at the sliding rotation or pivot point 26. For example, as shown in FIGS. 11 and 12 the second handle portion 20 and the second head portion 18 may be rotatably coupled via a screw, pin or like mechanism 54 that extends through nested or aligned apertures of the second handle portion 20 and the second head portion 18. The pin 54 and corresponding apertures may allow or provide relative rotational movement between the second handle portion 20 and the second head portion 18. As also shown in FIGS.

11 and 12, the aperture(s) of at least one of the second handle portion 20 and the second head portion 18 may be a slot 56 that is elongated along the length of the instrument 10 (or the length of the second handle portion 20 or the second head portion 18) to allow or provide relative translation or movement of the pin 54 therein, and thereby between the second handle portion 20 and the second head portion 18. The slot 56 may extend linearly, as shown in FIGS. 11 and 12. In some other embodiments, the slot 56 may extend non-linearly, such as an arcuate slot. The slot 56 may be oriented in any orientation so as to provide a desired relative motion between the second handle portion 20 and the second head portion 18, for example.

The pin 54 and the slot 56 may couple the second handle portion 20 and the second head portion 18 while allowing the ends thereof to converge and diverge as they rotate about the rotation or pivot point 22 and the rotation or pivot point 24, respectively As shown in FIG. 11, the pin 54 may be provided or positioned in a rearward portion of the slot 56 proximate to the free ends of the first and second handle portions 16, 20 in the open configuration of the instrument 10 (i.e., the open configuration first and second head portions 14, 18 and the first and second handle portions 16, 20). As shown in FIG. 12, the pin 54 may be provided or positioned in a forward portion of the slot 56 proximate to the first and second head portions 14, 18 in the closed configuration of the instrument 10 (i.e., the closed configuration first and second head portions 14, 18 and the first and second handle portions 16, 20). The pin 54 may thereby translate or move within the slot 56 to allow the second handle portion 20 and the second head portion 18 to rotate about the rotation or pivot point 22 and the rotation or pivot point 24, respectively, and remain coupled to each other. The pin 54 and the slot 56 may also thereby allow the cantilever motion between the first and second handle portions 16, 20 via the rotation or pivot point 22. In this way, the pin 54 and the slot 56 may cooperate to couple the second handle portion 20 and the second head portion 18, but allow or provide both relative rotational and translational movement between the second handle portion 20 and the second head portion 18 (while allowing rotational movement between the first and second handle portions 16, 20 via the rotation or pivot point 22 and the first and second head portions 14, 18 via the rotation or pivot point 24.

As also shown in FIGS. 1-4 and 8-10, a base or intermediate portion of the second head portion 18 that is positioned past or spaced from the rotation or pivot point 26 and the end portion thereof (that is rotatably or pivotally coupled to the second handle portion 20 at the rotation or pivot point 26) may be rotatably or pivotally coupled to a base or intermediate portion of the first head portion 14 of the first member 12 at a rotation or pivot point 24. The first head portion 14 and the second head portion 18 may be rotatably coupled at the rotation or pivot point 24 via any mechanism. For example, the first head portion 14 and the second head portion 18 may be rotatably coupled via a screw, pin or like mechanism that extends through nested or aligned apertures of the first head portion 14 and the second head portion 18, as shown in FIGS. 1-4 and 7-10. However, any other mechanism may be employed to rotatably or pivotally couple the first head portion 14 and the second head portion 18 at the rotation or pivot point 24.

Rotational or angular movement of the first and second handle portions 16, 20 (e.g., via manual manipulation thereof) with respect to each other (about the axis or point 22) between the open and closed configurations thereof may thereby effectuate corresponding rotational or angular movement of the first and second head portions 14, 18 with respect to each other (about the axis or point 24) between the open and closed configurations thereof via the rotation or pivot point 24. The closed configuration of the first and second handle portions 16, 20 may thereby correspond or effectuate the closed configuration of the first and second head portions 14, 18, and the open configuration of the first and second handle portions 16, 20 may thereby correspond or effectuate the open configuration of the first and second head portions 14, 18.

The portion of the second handle portion 20 extending between the free end thereof and the rotation or pivot point 22 may be substantially longer than the end portion thereof extending between the pivot point 22 and the rotation or pivot point 26. In this way, the second handle portion 20 may form a lever arm that acts to increase the mechanical advantage of the second handle portion 20 on the second head portion 18.

Figure 5:
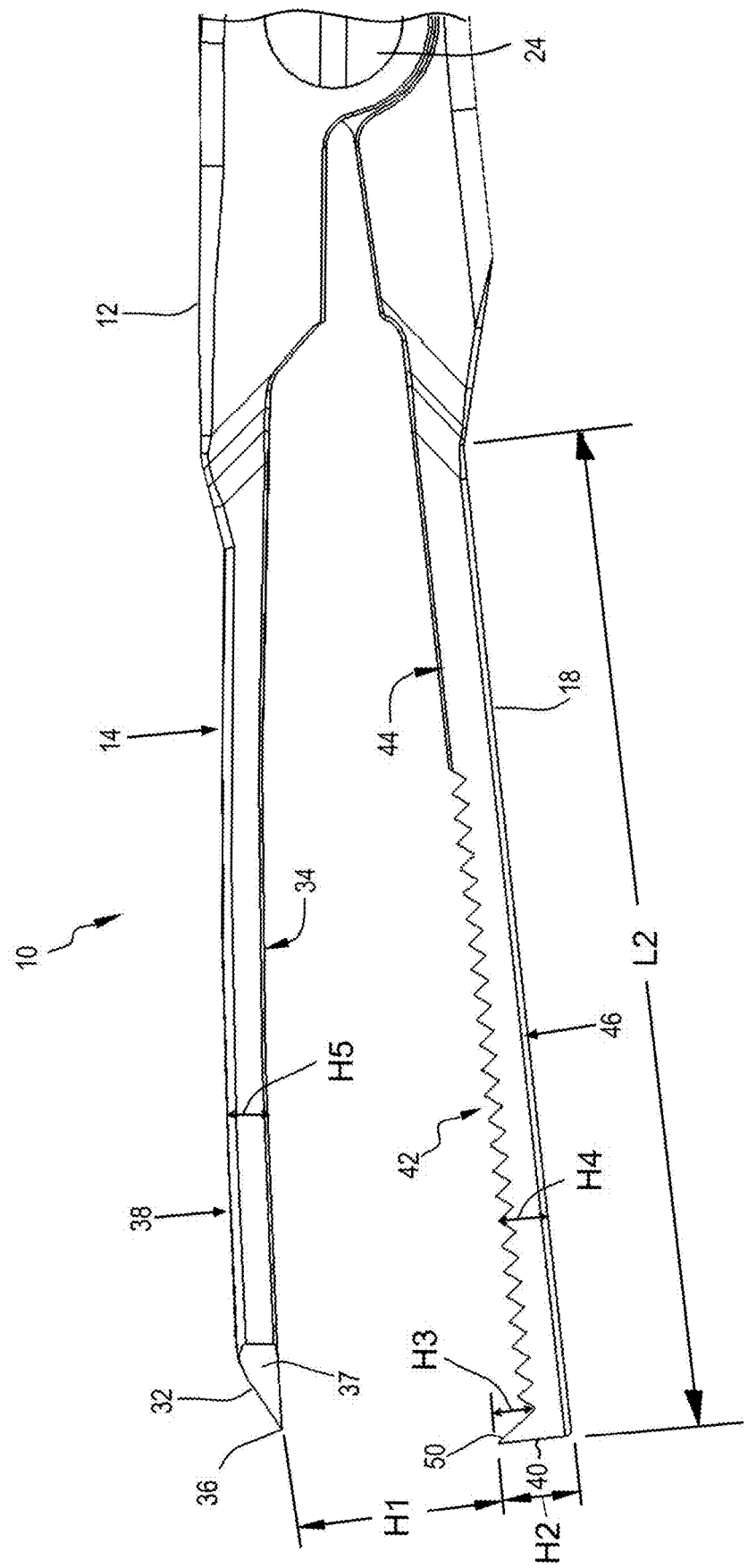
FIG. 5 is an enlarged side view of the head portion of the bone removal instrument of FIG. 1.

The first and second head portions 14, 18 may form mating jaws or the like (in the closed configuration) for engaging, potentially cutting, and removing bone and/or tissue. As shown in FIGS. 5, 9 and 10, the end portion of the first head portion 14 may be a relatively thin, narrow and flat elongate portion that forms a chisel or osteotome feature at the tip. For example, the free end or tip of the first head portion 14 may include a relatively sharp or pointed end or edge 36 at the junction of the inner surface 34 and outer surface 38 of the first head portion 14. A substantially flat (e.g., planar) and/or smooth chisel portion 32 of the outer surface 38 may extend away from the end or edge 36 to form a chisel tooth. The chisel portion 32 of the outer surface 38 may be angled with the interior surface 34 at an acute angle, such as within the range of about 15 degrees and about 75 degrees. The first head portion 14 may also include substantially flat (e.g., planar) and/or lateral side surfaces 37 that extend away from the end or edge 36 on the width or lateral sides thereof.

The inner surface 34 and/or outer surface 38 of first head portion 14 may be substantially smooth and/or planar, as shown in FIGS. 1-10. In some embodiments, the first head portion 14 may be slightly arcuate such that it curves toward the second head portion 18. The thickness or height H5 of the first head portion 14 may be relatively thin as shown in FIG. 5, such as within the range of about 0.5 mm and about 5 mm. The width W1 of the first head portion 14 may be relatively narrow as shown in FIG. 6, such as within the range of about 5 mm and about 20 mm. In one embodiment particularly well suited or advantageous for removing resecting bone and/or tissue during a Lapidus Arthrodesis procedure, for example, the thickness or height H5 of the first head portion 14 may be about 1.25 mm and the width W1 may be about 10 mm.

The length of the first head portion 14 may be slightly less than the length L2 of the second head portion 18, as shown in FIGS. 8-10. For example, as shown in FIGS. 5 and 10 the second head portion 18 may include a front tooth formed by a front face 40, a cutting edge 48 and a relief surface 50 extend from the cutting edge 48 at an angle (e.g., an acute angle) with respect to the front face 40 to a gullet. The instrument may be configured such that the front edge 36 of the first head portion 14 nests or abuts into the base of the relief surface 50 in the closed configuration, as shown in FIGS. 8-10. In some embodiments, the length L2 of the second head portion 18 may be within the range of about 10 mm and about 60 mm. In an embodiment particularly well suited or advantageous for removing resecting bone and/or tissue during a Lapidus Arthrodesis procedure, for example, the length L2 of the second head portion 18 may be about 32 mm.

The front face 40 and/or the relief surface 50 may be substantially flat (e.g., planar) and/or smooth. Similarly, the outer surface 46 of the second head portion 18 may be substantially flat (e.g., planar) and/or smooth. In some embodiments, the front face 40 and the outer surface 46 of the second head portion 18 may be oriented substantially perpendicular, as shown in FIGS. 5 and 10. With reference to FIG. 5, the thickness or height H2 of the front face 40 from the outer surface 46 to the cutting edge 48 (i.e., the thickness or height of the front tooth) of the second head portion 18 may be within the range of about 2 mm and about 6 mm, and the thickness or height H3 of the relief surface 50 from the cutting edge 48 to the deepest part of the gullet may within the range of about 1 mm and about 5 mm. In some embodiments, the length L2 of the second head portion 18 may be within the range of about 10 mm and about 60 mm. In an embodiment particularly well suited or advantageous for removing resecting bone and/or tissue during a Lapidus Arthrodesis procedure, for example, the thickness or height H2 of the front face 40 may be about 2.25 mm, and the thickness or height H3 of the relief surface 50 may be about 1.25 mm.

The interior of the second head portion 18 may include a series or plurality of gripping teeth 42 extending from the relief surface 50 of the front tooth, as shown in FIGS. 1-10. As shown in FIGS. 5 and 10, each of the gripping teeth 42 may include front faces, tips or top edges, and relief surfaces extending from the tips or top edges to form a gullet. The gripping teeth 42 may be relatively smaller and lower than the front tooth. For example, the thickness or height H4 of the tips or top edges of the gripping teeth 42 measured from the outer surface 46 (i.e., the thickness or height of the gripping teeth 42) of the first head portion 14 may be within the range of about 1 mm and about 5 mm, as shown in FIG. 5. In an embodiment particularly well suited or advantageous for removing resecting bone and/or tissue during a Lapidus Arthrodesis procedure, for example, the thickness or height H4 of the gripping teeth 42 may be about 1.5 mm The inner surface of the second head portion 18 may include a substantially flat or planar surface 44 extending from the gripping teeth 42 toward the rotation or pivot point 24, as shown in FIGS. 1-5 and 8-10. In the fully closed orientation as shown in FIG. 10, the instrument 10 may form a gap between the inner surfaces of the first and second head portions 14, 18 that narrows or thins from a thickness H6 between the inner surface 34 of the first head portion 14 and the flat inner surface 44 of the second head portion 18 to the junction of the chisel edge 36 of the first head portion 14 and the relief surface 50 of the front tooth of the second head portion 18. In some embodiments, the thickness H6 between the inner surface 34 of the first head portion 14 and the flat inner surface 44 of the second head portion 18 in the fully closed orientation of the instrument 10 may be within the range of about 1 mm and about 5 mm, as shown in FIG. 10. In an embodiment particularly well suited or advantageous for removing resecting bone and/or tissue during a Lapidus Arthrodesis procedure, for example, the thickness H6 between the inner surface 34 of the first head portion 14 and the flat inner surface 44 of the second head portion 18 in the fully closed orientation of the instrument 10 may be about 2.5 mm.

In the fully open orientation or state as shown in FIG. 5, the instrument 10 may form a gap between the inner surfaces of the first and second head portions 14, 18 that narrows or thins from a height or distance H1 measured between the chisel edge 36 of the first head portion 14 and the cutting edge 40 of the front tooth of the second head portion 18 to the mechanism forming the rotation or pivot point 24. In some embodiments, the height or distance H1 measured between the chisel edge 36 of the first head portion 14 and the cutting edge 40 of the front tooth of the second head portion 18 in the fully open orientation or state of the instrument 10 may be within the range of about 3 mm and about 20 mm, as shown in FIG. 5. In an embodiment particularly well suited or advantageous for removing resecting bone and/or tissue during a Lapidus Arthrodesis procedure, for example, the height or distance H1 measured between the chisel edge 36 of the first head portion 14 and the cutting edge 40 of the front tooth of the second head portion 18 in the fully open orientation or state of the instrument 10 may be about 11 mm.

Figure 13:
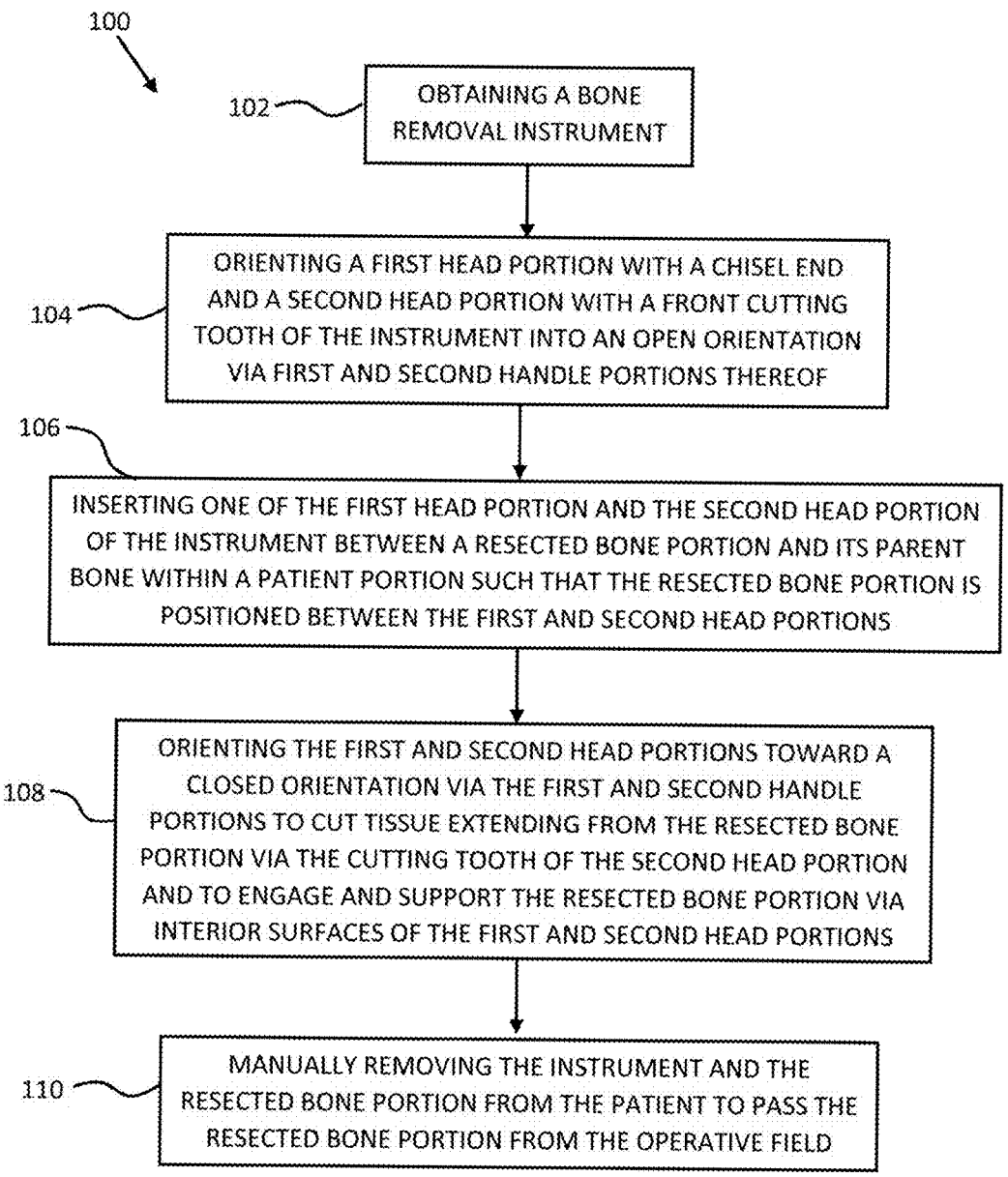
FIG. 13 is a flow chart illustrating a method of removing a resected bone portion from a patient.

As depicted in the flow chart in FIG. 13, the present disclosure methods 100 for removing a resected bone portion from a patient. The methods 100 may include obtaining 102 the instrument 10 described above and shown in FIGS. 1-12, and manually configuring or orienting 104 the instrument 10 into an at least partially opened orientation or state via the first and second handle portions 16, 20, as depicted in FIG. 13. The first head portion 14 of the instrument 10 may then be manually inserted 106 (via the first and second handle portions 16, 20) between a resected bone portion (e.g., a relatively thin bone wafer) and its parent bone portion such that the resected bone portions is positioned between the first and second head portions 14, 18, as depicted in FIG. 13. Alternatively, the second head portion 18 of the instrument 10 may be manually inserted 106 (via the first and second handle portions 16, 20) between a resected bone portion (e.g., a relatively thin bone wafer) and its parent bone portion such that the resected bone portions is positioned between the first and second head portions 14, 18. The resected bone portion may include cartilage, other tissue extending therefrom and/or subchondral bone. The first head portion 14 of the instrument 10 may be manually inserted 106 (via the first and second handle portions 16, 20) between the resected bone portion (e.g., a relatively thin bone wafer) and the parent bone portion to such an extent that the cutting edge 48 of the second head portion 18 is positioned at least past the deepest adjacent bone surface of the resected bone portion.

With the cutting edge 48 of the second head portion 18 positioned at least past the deepest adjacent bone surface of the resected bone portion, the instrument 10 may be manually reoriented or reconfigured 108 via the first and second handle portions 16, 20 toward the fully closed orientation or state, as depicted in FIG. 13. Movement 108 of the instrument from the opened orientation toward the closed orientation may cause the cutting edge 48 of the second head portion 18 to interact with and thereby cut or separate one or more tendon, ligament or other tissue extending from the adjacent bone surface of the resected bone portion (i.e., the outer or distal end of the parent bone prior to resection), if present. Further, movement 108 of the instrument from the opened orientation toward the closed orientation may cause the substantially flat and/or smooth inner surface 34 of the first head portion 14 to engage and support the substantially flat and/or smooth resected surface of the resected bone portion, and the gripping teeth 42 and substantially flat and/or smooth inner surface 44 of the second head portion 14 to engage and support the outer surface of the resected bone portion opposing the resected surface (which may be non-planar and/or rough). The instrument 10 may thereby prevent cracking or crumbling of the resected bone portion, such as when the resected bone portion is in the form of a wafer. Once the resected bone portion is engaged and supported by the first and second head portions 14, 18, the instrument 10 and the resected bone portion may be manually removed or pulled 110 from the patient via the first and second handle portions 16, 20 to pass the resected bone portion from the operative field, as depicted in FIG. 13.

In some embodiments, the method 100 may include removing a resected bone portion from a patient may during a Lapidus Arthrodesis procedure. For example, an incision may be generally made longitudinally over a $1^{st}$ tarsometatarsal joint ($1^{st}$ TMTJ) of a patient. Soft tissue dissection may be performed to expose the $1^{st}$ TMTJ. After exposure of the joint surfaces at the $1^{st}$ TMTJ, cartilage resection may be performed. Cartilage may be resected from the $1^{st}$ metatarsal base first, such as if the surgeon prefers to use a sagittal saw for the resection of the cartilage.

A sagittal saw may then be used to resect an approximate 2 mm thick wafer of bone that contains cartilage and a small amount of subchondral bone at the base of the $1^{st}$ metatarsal. The arcuate, smooth first head portion 14 of the instrument 10 containing the chisel tooth 36 may be inserted where the sagittal saw made a cut, with the substantially flat, sharp second head portion 18 of the instrument 10 containing the cutting edge 48 and front tooth inserted into the $1^{st}$ tarsometatarsal joint. Alternatively, the substantially flat, sharp second head portion 18 of the instrument 10 containing the cutting edge 48 and front tooth may be inserted where the sagittal saw made a cut, with the arcuate, smooth first head portion 14 of the instrument 10 containing the chisel tooth 36 inserted into the $1^{st}$ tarsometatarsal joint. The instrument 10 may be inserted in a partially opened orientation. The position and orientation of the instrument 10 during insertion may be generally dorsomedial to plantarlateral. However, the position and orientation of the instrument 10 during insertion may be generally dorsal to plantar or medial to lateral across the joint.

When the surgeon feels that the instrument 10 is fully inserted to where the cutting edge 48 of the front tooth of the second head portion 18 is positioned just past the bone surface on the opposite side, the instrument 10 may be closed as much as possible via the first and second handle portions 16, 20. The cutting edge 48 of the front tooth of the second head portion 18 may cut or separate the insertion of the tibialis anterior tendon and other ligaments from the resected wafer bone portion with the gripping teeth 42 and the substantially flat and/or smooth interior surfaces 34, 44 of the first and second head portions 14, 18 of the instrument 10 grasping and supporting the flat surfaces of resected wafer bone portion with a relatively low risk of cracking or crumbling the wafer. The instrument 10 and the resected wafer bone portion may then be removed from the joint and the resected wafer bone portion passed from the operative field.

The sagittal saw may then be used to make a cut along the medial cuneiform, resecting approximately 2 mm of bone medially up to approximately 4 mm of bone laterally if angular correction is desired, forming another resected wafer bone portion. The arcuate, smooth first head portion 14 of the instrument 10 containing the chisel tooth 36 may be inserted where the sagittal saw made a cut, with the substantially flat, sharp second head portion 18 of the instrument 10 containing the cutting edge 48 and front tooth inserted into the $1^{st}$ tarsometatarsal joint. Alternatively, the substantially flat, sharp second head portion 18 of the instrument 10 containing the cutting edge 48 and front tooth may be inserted where the sagittal saw made a cut, with the arcuate, smooth first head portion 14 of the instrument 10 containing the chisel tooth 36 inserted into the $1^{st}$ tarsometatarsal joint. The position and orientation of the instrument 10 during insertion may be generally dorsomedial to plantarlateral. However, the position and orientation of the instrument 10 during insertion may be generally dorsal to plantar or medial to lateral across the joint.

When the surgeon feels that the instrument 10 is fully inserted to where the cutting edge 48 of the front tooth of the second head portion 18 is positioned just past the bone surface on the opposite side, the instrument 10 may be closed as much as possible via the first and second handle portions 16, 20. The cutting edge 48 of the front tooth of the second head portion 18 may cut or separate the tibialis anterior tendon and other ligaments from the resected wafer bone portion with the gripping teeth 42 and the substantially flat and/or smooth interior surfaces 34, 44 of the first and second head portions 14, 18 of the instrument 10 grasping and supporting the flat surfaces of resected wafer bone portion. The instrument 10 and the resected wafer bone portion may then be removed from the joint and the resected wafer bone portion passed from the operative field.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A surgical instrument, comprising:
   a first elongate member including a first head portion and a first handle portion defining a free end, the first head portion being elongated along a length direction and including a front edge defining a free end of the first head portion along the length direction;
   a second elongate member rotatably coupled to the first elongate member at a first rotation point, the second member including a second handle portion defining a free end and an end portion on opposing sides of the first rotation point; and
   a third elongate member rotatably coupled to the first elongate member at a second rotation point, the third member including a second head portion being elongated along the length direction and an end portion on opposing sides of the second rotation point,
   wherein the end portions of the second and third members are rotatably coupled at a third movable rotation point positioned between the first and second rotation points,
   wherein the second head portion includes an interior surface with a front cutting tooth comprising a front face that defines a free end of the second head portion along the length direction, a cutting edge at a top end of the front face, and a relief surface that extends from the cutting edge at an acute angle with respect to the front face,
   wherein the first head portion comprises a substantially smooth interior tissue engagement surface extending from the front edge, and a chisel portion extending from the front edge at an acute angle with respect to the interior tissue engagement surface, wherein the interior tissue engagement surface, the chisel portion and the front edge form a chisel tooth with the front edge being a tip of the chisel tooth,
   wherein the front cutting tooth is extended along a width direction such that the cutting edge is extended along the width direction, and the chisel tooth is extended along the width direction such that the front edge is extended along the width direction, and
   wherein the second head portion extends further along the length direction than the first head portion such that, in a fully closed relative position of the first and second head portions, the front edge of the chisel tooth abuts the relief surface of the front cutting tooth.

2. The instrument of claim 1, wherein the interior tissue engagement surface is substantially planar along the width and length directions.

3. The instrument of claim 1, wherein the interior tissue engagement surface is arcuate and curves toward the second head portion as it extends toward the front edge.

4. The instrument of claim 1, wherein the interior surface of the second head portion includes a substantially smooth tissue engagement surface and a plurality of teeth extending between the front cutting tooth and the tissue engagement surface of the interior surface of the second head portion.

5. The instrument of claim 4, wherein the front cutting tooth is taller than the plurality of teeth.

6. The instrument of claim 4, wherein the substantially smooth interior tissue engagement surface of the first head portion and the plurality of teeth of the interior surface of the second head portion are configured to engage and support a resected tissue portion.

7. The instrument of claim 1, wherein the second head portion extends further from the second rotation point than the first head portion.

8. The instrument of claim 7, wherein the length of the second head portion is within the range of 10 mm and 60 mm.

9. The instrument of claim 1, wherein the first and second head portions define a width within the range of 5 mm and 20 mm.

10. The instrument of claim 1, wherein the first head portion defines a thickness within the range of 0.5 mm and 5 mm, and the front cutting tooth of the second head portion defines a thickness within the range of 2 mm and 6 mm.

11. The instrument of claim 1, wherein, in a fully closed relative position of the first and second handle portions, the front edge abuts the second head portion.

12. The instrument of claim 11, wherein, in the fully closed relative position of the first and second handle portions, the first and second head portions form a gap therebetween that enlarges as it extends from the front edge toward the second rotation point.

13. The instrument of claim 1, wherein, in an open relative position of the first and second handle portions, the front edge is spaced from the front cutting tooth a distance within the range of 3 mm and 20 mm.

14. The instrument of claim 13, further comprising a biasing mechanism that biases the first and second handle portions into the open position in a neutral state of the instrument.

15. The instrument of claim 1, wherein the movable rotation point is formed via a pin member extending through an aperture of one of the end portions of the second and third members and a slot of the other of the end portions.

16. The instrument of claim 1, wherein the interior surface of the second head portion includes a substantially flat tissue engagement surface.

17. The instrument of claim 1, wherein the cutting edge is extended substantially linearly along the width direction, and the front edge is extended substantially linearly along the width direction.

18. The instrument of claim 1, wherein at least one of the front face and the relief surface is a three-dimensional planar surface.

19. The instrument of claim 1, wherein the substantially smooth interior tissue engagement surface is planar along the width direction and substantially smooth along the length direction.

20. The instrument of claim 1, wherein, in the fully closed relative position of the first and second head portions, the cutting edge of the front cutting tooth is positioned past the front edge of the chisel tooth in both the length direction and a thickness direction extending away from the interior surface of the second head portion.

21. A method of removing a resected tissue portion from a body, comprising:
obtaining a tissue removal instrument comprising:
a first elongate member including a first head portion and a first handle portion defining a free end, the first head portion being elongated along a length direction and including a front edge defining a free end of the first head portion along the length direction;
a second elongate member rotatably coupled to the first elongate member at a first rotation point, the second member including a second handle portion defining a free end and an end portion on opposing sides of the first rotation point; and
a third elongate member rotatably coupled to the first elongate member at a second rotation point, the third member including a second head portion being elongated along the length direction and an end portion on opposing sides of the second rotation point,
wherein the end portions of the second and third members are rotatably coupled at a third movable rotation point positioned between the first and second rotation points,
wherein the second head portion includes an interior surface with a front cutting tooth comprising a front face that defines a free end of the second head portion along the length direction, a cutting edge at a top end of the front face, and a relief surface that extends from the cutting edge at an acute angle with respect to the front face,
wherein the first head portion comprises a substantially smooth interior tissue engagement surface extending from the front edge, and a chisel portion extending from the front edge at an acute angle with respect to the interior tissue engagement surface, wherein the interior tissue engagement surface, the chisel portion and the front edge form a chisel tooth with the front edge being a tip of the chisel tooth,
wherein the front cutting tooth is extended along a width direction such that the cutting edge is extended along the width direction, and the chisel tooth is extended along the width direction such that the front edge is extended along the width direction, and
wherein the second head portion extends further along the length direction than the first head portion such that, in a fully closed relative position of the first and second head portions, the front edge of the chisel tooth abuts the relief surface of the front cutting tooth, the first and second handle portions configured to effectuate relative movement of the first and second head portions between an open position and the fully closed relative position;
orienting the first and second head portions of the instrument into the open position via the first and second handle portions;
inserting one of the first head portion or the second head portion between the resected tissue portion and a host tissue portion within the body such that the resected tissue portion is positioned between the first and second head portions of the instrument;
orienting the first and second head portions of the instrument toward the fully closed relative position via the first and second handle portions to cut tissue extending from the resected tissue portion via the front edge of the first head portion and the front cutting tooth of the second head portion and to engage and support the resected tissue portion via the interior surfaces of the first and second head portions; and
manually removing the instrument and the resected tissue portion from the body.

22. The method of claim 21, wherein the interior surface of the second head portion includes a substantially flat tissue engagement surface and plurality of teeth extending between the front cutting tooth and the substantially flat tissue engagement surface.

23. The method of claim 21, wherein the resected tissue portion is a bone wafer.

24. The method of claim 23, wherein the host tissue portion is a 1$^{st}$ metatarsal bone.

25. The method of claim 24, wherein the cut tissue comprises a tibialis anterior tendon.

26. The method of claim 21, wherein the interior surface of the second head portion includes a plurality of teeth, and wherein the substantially smooth interior tissue engagement surface of the first head portion and the plurality of teeth of the interior surface of the second head portion are configured to engage and support the resected tissue portion.

* * * * *